United States Patent
Neuberger et al.

[11] Patent Number: 6,056,548
[45] Date of Patent: May 2, 2000

[54] HYGIENIC DENTAL LASER PHOTO TREATMENT METHOD

[75] Inventors: Wolfgang Neuberger, F. T. Labuan, Malaysia; Walter Cecchetti, Saonara, Italy

[73] Assignee: CeramOptec Industries, Inc., East Longmeadow, Mass.

[21] Appl. No.: 09/277,017

[22] Filed: Mar. 26, 1999

Related U.S. Application Data

[63] Continuation-in-part of application No. 08/914,453, Aug. 19, 1997, abandoned, and a continuation-in-part of application No. 08/429,083, Apr. 26, 1995, Pat. No. 5,658,148.

[51] Int. Cl.[7] ............................................. A61C 5/00
[52] U.S. Cl. ............................................. 433/215; 433/216
[58] Field of Search ..................... 433/29, 215, 216; 606/13, 15, 16, 17; 607/89

[56] References Cited

U.S. PATENT DOCUMENTS

| | | | |
|---|---|---|---|
| 4,952,143 | 8/1990 | Becker et al. | 433/215 |
| 5,032,178 | 7/1991 | Cornell . | |
| 5,098,303 | 3/1992 | Fischer | 433/215 |
| 5,207,576 | 5/1993 | Vassiliadis et al. | 433/215 |
| 5,306,143 | 4/1994 | Levy | 433/29 |
| 5,611,799 | 3/1997 | Wilson et al. . | |
| 5,622,501 | 4/1997 | Levy | 433/216 |
| 5,645,428 | 7/1997 | Yarborough | 433/215 |
| 5,658,148 | 8/1997 | Neuberger et al. . | |
| 5,713,738 | 2/1998 | Yarborough | 433/215 |
| 5,766,011 | 6/1998 | Sibner | 433/215 |
| 5,785,527 | 7/1998 | Jensen et al. | 433/215 |
| 5,800,165 | 9/1998 | Kirsch et al. | 433/215 |

FOREIGN PATENT DOCUMENTS

WO/93/21992  11/1993  WIPO ..................................... 607/89

OTHER PUBLICATIONS

Guliana Valduga et al. "F2 of Extracellularly Generated Singlet Oxygen on Gram–positive & Gram–negative Bacteria" J. Photochem. Photobiol. B: Biol 21 81–86 (1993).

*Primary Examiner*—Ralph A. Lewis
*Attorney, Agent, or Firm*—Bolesh J. Skutnik; BJ Associates

[57] ABSTRACT

The invention is a safe, hygienic method to use a laser toothbrush employing low power radiation in conjunction with an enhanced dental liquid or paste. The method provides a safe hygienic dental treatment that can be practiced by anyone and enhances destruction of oral viruses and bacteria. The present invention teaches a method which will have a significant effect on the treatment of all types of oral diseases, inflammations, and infections. A pulsed diode laser as well as a continuous wave diode laser can be used with an enhanced dental liquid or paste for selective biostimulation within the oral cavity with little more effort than a conscientious person spends brushing their teeth.

18 Claims, 4 Drawing Sheets

HYGIENIC DENTAL LASER PHOTO TREATMENT METHOD

REFERENCE TO RELATED CASE

This application is a continuation-in-part of co-pending U.S. patent application Ser. No. 08/914,453 filed on Aug. 19, 1997 by Wolfgang Neuberger and Walter Cecchetti, inventors, entitled "DENTAL LASER PHOTO TREATMENT AND METHOD" which in turn was a continuation-in-part of U.S. patent application Ser. No. 08/429,083 filed on Apr. 26, 1995 by Wolfgang Neuberger and Walter Cecchetti, inventors, entitled "DENTAL LASER BRUSHING OR CLEANING DEVICE", now issued as U.S. Pat. No. 5,658,148, and incorporated by reference herein.

BACKGROUND OF THE INVENTION

1. Field of the Invention

The invention relates generally to a new hygienic treatment method for dental care in which a laser toothbrush is employed on a regular schedule with lightly photosensitized liquids or paste to achieve and maintain a reduction in bacteria in the oral cavity while minimizing side effects of photosensitizers.

2. Invention Disclosure Statement

Generally in the prior art mechanical cleaning of teeth with manual, electric and/or water jet devices is of a superficial nature only and does not penetrate into the skin-tissue or into pockets to remove or destroy bacteria and viral contamination. Additionally, normal dental paste is of very limited effect in terms of bacterial and viral destruction. Low power laser bio-stimulation produces enzymes which can destroy viruses and bacteria present on teeth, in the mouth, on the gums and below the gum line. Consequential inflammation and pain is also eliminated. The radiation must be provided with pulsed diode laser at varying repetition rate frequencies to selectively trigger the body's natural defense to infection within the mouth. Optimum effect can be achieved with GaAs (Gallium Arsenide) pulsed diode laser at a width of 200–300 nsec, $\lambda=904$ nm, power=5–10 mW, application time 1–3 minutes. Three different repetition rate frequencies can be used to treat different dental conditions as follows:

F1=73 Hz for Parodontitides, dental pain

F2=292 Hz for Gingivitis, stomatitis

F3=584 Hz for Gingivitis, stomatitis paradontophaties

It is known through research in the area of photodynamic therapy that certain substances are created as a byproduct of laser radiation. These substances contain atomic or singlet oxygen that is believed to destroy tumor cells. Similarly, atomic oxygen resulting from laser radiation can enhance destruction of oral bacteria and viruses. Research has been conducted and reported which teaches that gram-positive and gram-negative bacteria are sensitive to singlet oxygen generated by a physically separated photosensitizer. Thus, laser radiation will destroy oral bacteria. [See, e.g., Giuliana Valduga et. al., "Effect of Extracellularly Generated Singlet Oxygen on Gram-positive and Gram-negative Bacteria," *J. Photochem. Photobiol. B. Biol.*, 21 (1993) 81–86.]

The wavelength at which the diode laser of the system is operated is related to the specific photosensitizer used. A photosensitizer such as a Phthalocyanine can be activated by continuous wave diode laser as follows:

(a) Zn (II) phthalocyanine is activated at $\lambda=670$ nm (b) Si (IV) naphthalocyanine is activated at $\lambda=780$ nm (c) Pd $(OBu)_8$ naphthalocyanine is activated at $\lambda=820$ nm These methods and practices need to be performed by trained professionals, thus they cannot be part of a routine dental hygiene approach. They are both cost and time prohibitive because they must be done in a dental practitioners office.

Besides the phthalocyanine photosensitizers, described above, other sensitizers such as methylene blue are used for PhotoDynamic and similar therapies. For example in Wilson et al., U.S. Pat. No. 5,611,793, a large number of chemical which disinfect or sterilize tissues within the oral cavity and are activated by laser light are described and their relative efficiency of action measured.

Generally as in U.S. Pat. No. 5,611,793 the treatment, as with the earlier described laser treatments, is provided by a professional frequently in combination with some dental surgical procedures. Highly active materials are used to provide for quick treatment times or else intense sources are needed to allow professionals to see multiple patients in a given working period. The need for dental practitioners is due primarily to two major safety problems. First, because of the intensity of coherent laser light the possibility for accidental injury arises from misapplication or misdirection of the laser output. Temporary or permanent damage to unprotected eyes can occur as well as 'burning' of healthy tissue instead of attack on diseased tissue only. Tissue damage can occur because the photosensitizers while somewhat selective usually are taken up by healthy tissue as well as diseased tissue. Secondly, ingestion of these sensitizers, accidental or otherwise, creates potential for serious side effects such as 'sun burning' of the skin upon exposure to normal sunlight or even bright lights. Often significant levels of the photosensitizer need to be associated with a treatment site for the PDT process to be effective. Should a patient swallow a significant amount of the photosensitized material they would have to restrict their exposure to daylight for a period of a few hours to a few days to allow time for the photosensitizers to be expelled from normal tissue and eventually the body. For general use by the public, accidental ingestion by a child would be an added safety concern. These safety concerns are now ameliorated by requiring the use of trained dental practitioners generally in a remote site for such treatments. It would be a gain in the public's dental care if the benefits of such processes could be made more wide spread.

In addition multiple treatments with photosensitizers, which are at the levels needed for PDT treatments and which actively absorb light in the visible region of the spectrum, can lead to incorporation of the colored segments into the enamel or dentin. While there are many bleaching compositions and methods available, see e.g. Cornell U.S. Pat. No. 5,032,178 they can be time consuming or require careful application.

The present invention presents methods to avoid or ameliorate these problems by providing safe, simple methods for improved dental care by the 'patient' consumers themselves. The methods and devices described herein provide a general dental hygiene program which allow the public user to maintain better oral hygiene with reduced bacterial and microbial contamination within the oral cavity, and thus to enjoy the health and other benefits arising from the cleaner oral environment.

BRIEF SUMMARY OF THE INVENTION

It is an aim of the present invention to address the need for an general hygienic oral treatment or cleaning method which will have a significant destructive effect on bacteria, viruses and other microbes, and be safe enough for use by the public.

It is a further aim of the present invention to provide a dental liquid or paste to be used with a dental laser brushing system and which contains photosensitizer(s) to increase the destructive effects on bacteria and viruses through multi-day in-home applications, without the deleterious side effects of the photosensitizers to exposure to the sun and bright lights.

It is yet another aim of the present invention to provide a system to permit the delivery of low power radiation through a liquid jet or jets within the system to activate the enhanced dental liquid or paste including whitening agents present.

Briefly stated, in the present invention a safe, hygienic method to use a laser toothbrush providing low power radiation in conjunction with an enhanced dental liquid or paste is described. The method provides a safe hygienic dental treatment that can be practiced by anyone and enhances destruction of oral viruses and bacteria. The present invention teaches a method which will have a significant effect on the treatment of all types of oral diseases, inflammations, and infections. A pulsed diode laser as well as a continuous wave diode laser can be used with an enhanced dental liquid or paste for selective bio-stimulation within the oral cavity with little more effort than a conscientious person spends brushing their teeth.

The above, and other objects, features and advantages of the present invention will become apparent from the following description read in conjunction with the accompanying drawings.

DETAILED DESCRIPTION OF THE PREFERRED EMBODIMENT(S)

Figure 1:
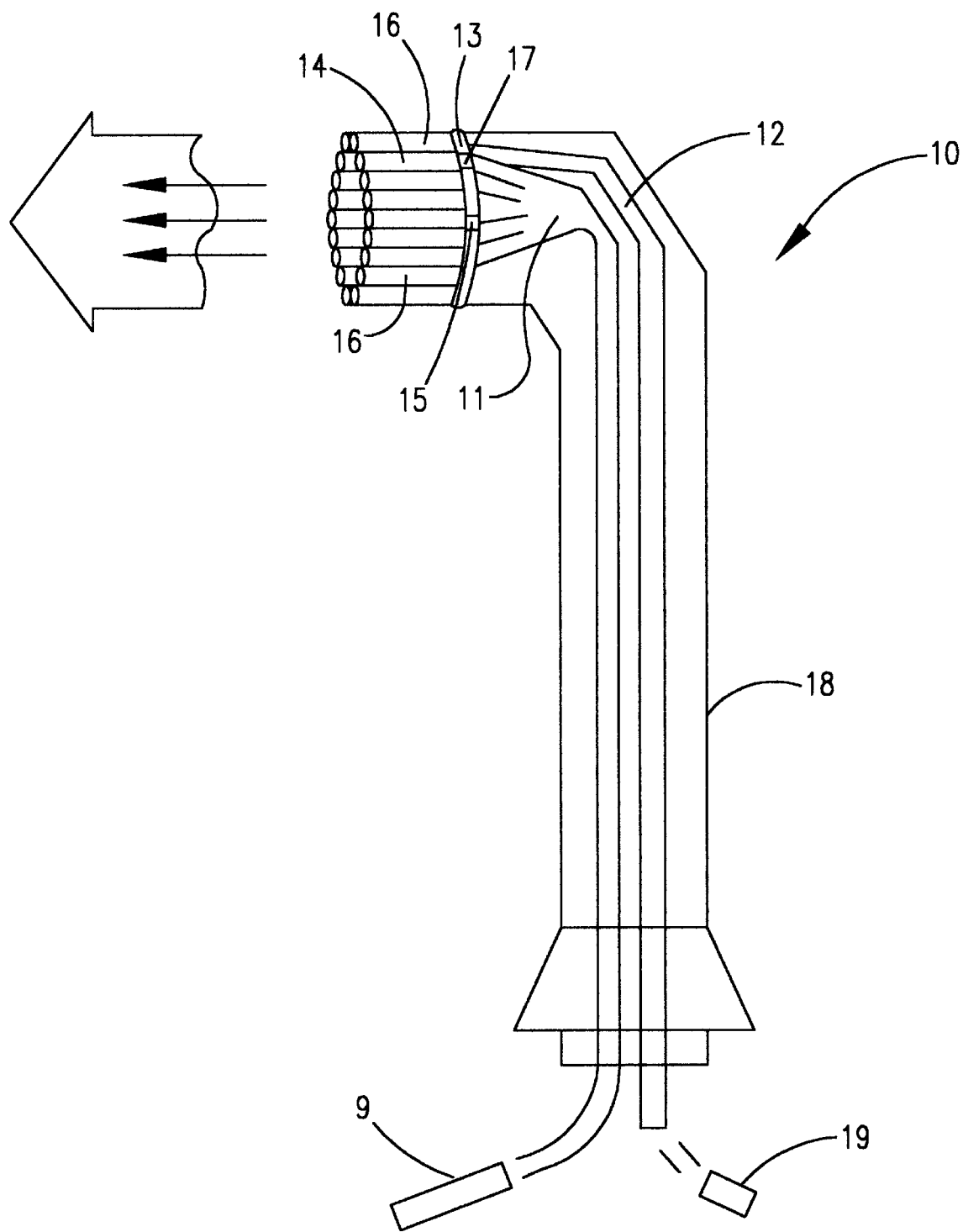
FIG. 1 is a view if the end of the mechanical oral cleaning system showing a circular fixed tip, optical fibers and liquid jets within the brushhead for laser radiation delivery that can be used with the invented method.

In the prior art, summarized earlier, most applications of PhotoDynamic Therapy (PDT) involve ingestion or the separate application of a chemical that is photoactivated to create an excited state that reacts with available oxygen to form atomic singlet oxygen as noted in the background. The active chemicals are often referred to as photosensitizers and commonly have molecular structures which incorporate light absorbing species much like a dye molecule.

Along with the safety and cost problems identified earlier, after multiple treatments with photosensitized dental liquids or pastes, teeth can become colored due to incorporation of sensitizers or sensitizer fragments into the enamel or dentin. In principle this can occur with all photosensitizers because as a class they are dyes. Coloring or staining of teeth is thus a deleterious side effect of treatments by PDT. The present invention discloses several ways to gain the benefits of PDT type oral treatments while removing the need to have the treatments performed by a dental practitioner and including ways of minimizing the coloring problem.

In the present invention, a surprisingly simple and safe method of treatment is provided for use by the general public in conjunction with the devices described originally in the parent application Ser. No. 08/429,083, now U.S. Pat. No. 5,658,148, and further described below. A home dental treatment is described that consumers can use with associated dental preparations and special laser toothbrushes to improve their total oral hygienic approach to dental care.

It has been found that benefits of reduced presence of bacteria and other microbes on teeth and in the oral cavity can be achieved by a general user [consumer] through a low power application of laser radiation in conjunction with a dilute mixture of photosensitizers in a dental paste or liquid. By keeping the power at below 10 mW and preferably below 5 mW and using a diode laser source emitting wavelengths substantially the same as the absorption wavelength of the photosensitizers, non-professional people can initiate quasi-PDT processes within their oral cavities in a safe manner, thus improving their oral/dental hygiene. The process depends also on a regular scheduled application of the method with the specially prepared dental pastes or liquids over an extended period of time. The surprising result is that many of the results of PDT treatments can be effected by the use of very low power irradiations of mixtures containing highly diluted photosensitizers. An example follows the description of the figures.

The general consumer would now have the opportunity for the first time to really obtain and maintain a cleaner hygienic environment with their oral cavities. The method is similar to the normal tooth brushing techniques so that the user can easily adapt his normal routines to gain the benefits of this invention. Particularly when used with the laser tooth brushes described herein, the process is safe, easy and effective. Doses, i.e. power [mwatts] and treatment time, are in the range where prior art such as Wilson et al. would state treatments were ineffectual. By making the system of laser toothbrush, dental liquids, pastes and method of operation simple, the consumer can self-treat themselves in a safe, effective and commercially viable package.

As an added feature to reduce the possibility of discoloration of teeth, a two step process can be used, where first the bacteria are partially destroyed by the application and activation of a photosensitized liquid or paste and secondly, the residual photosensitizer is degraded. A dental liquid or paste containing photosensitizer is applied to the area to be treated which is then subjected to illumination by a system which can direct the light onto the treated area. After allowing treatment to occur, a second 'whitening' paste or liquid is applied that degrades all residual photosensitizer. For example, degradation of the photosensitizer can be performed with hydrogen peroxide ($H_2O_2$) which is incorporated into a whitening paste or fluid, which adds some of the benefits of the prior art to the present invention.

As an alternative in the direct method, an accelerated degradation/destruction of the photosensitizer, enhanced whitening, can occur if one can take advantage of photobleaching effects. Photobleaching of dyes generally involves illumination in the presence of oxygen, as for example sunlight illumination of colored materials/clothes. The oxygenation reaction, which degrades the dye, is activated by the energy of photons that are irradiated within the absorption band of the dye.

A treatment procedure can involve two illumination steps. First a therapeutically active illumination wavelength, which is optimized for the PDT effect, is applied and the bacteria are destroyed. A second bleaching illumination wavelength, which is optimized for destroying the sensitizer, is applied and the treated area rinsed clean.

For many photosensitizers, in their functioning to activate a therapeutic action they are themselves photodegraded by the therapeutic illumination wavelength. This natural benefit can be enhanced by the addition of a bleach enhancing oxygen donor such as hydrogen peroxide. The concentration of the bleach enhancing substance is adjusted so that after the time needed for optimal bacteria destruction, the sensitizer is also bleached nearly completely by continued irradiation and thus does not cause colored teeth. This is essentially a one illumination step, although the irradiation intensity might be modified in some cases for the two processes to occur in an optimal fashion. For example, a low intensity or short burst of light could be used to activate the generation of singlet oxygen to kill the bacteria and then a higher intensity or longer burst of light could be used to destroy any remnant sensitizer.

Another way to improve the effectiveness of the present invention is to simultaneously improve destruction of bacteria and reduce side effects of the use of photosensitizers with a process improvement that can improve the efficiency and selectivity of the sensitizer's ability to destroy bacteria by employing a carrier system. Higher efficiency means less sensitizer is needed and milder treatment conditions can be employed, or there can be longer periods between treatments. Here the sensitizer is chemically, loosely bound to a carrier, like an antibody. When the carrier contacts the bacteria, the sensitizer can adhere to the bacterial surface or can be incorporated by the bacteria causing the sensitizer to approach the bacteria's nucleus more closely. During the irradiation with the therapeutic wavelength, the RNA of the bacteria can be effectively oxidized by the catalytic effect of the photosensitizer.

The easier way to visualize the method is to describe a few of the laser toothbrushes that are preferred to be used with the method along with some of the brushes special features. The following descriptions are of systems to transmit and direct treatments of the present invention onto teeth or other oral cavity areas which would benefit by treatment. For a majority of users the treatment of teeth and the reduction bacterial, and other microbial contamination on them and the gum area is the primary use of the invented method, thus, brushlike devices are primarily described. Using the dental liquid alternative a simpler tool holding at least on optical fiber might also be used to transmit and direct therapeutic illumination onto an oral cavity site requiring treatment. For example a tube having a slight bend at its distal end would house a fiber or fiber bundle through which the therapeutic wavelength illumination is transmitted to the treatment site. The liquid would be forced under pressure to bring the photosensitized mixture to the treatment areas.

FIG. 1 shows a preferred embodiment of a system to use with the invention in which plastic brush 10 with handle 18 contains one or more optical fiber 11s and water or liquid passage 12. Optical fibers 11 carry radiation from a radiation source, not pictured, to brushhead 13, and water or liquid passage 12 carries water or liquid under pressure to brushhead 13. Optical fibers 11 may be optically connected to one or more optical bristle(s) 14, which deliver radiation to the areas in the mouth being cleaned through those bristle 14 ends not optically connected to optical fibers 11. Optical fibers 11 may also terminate in one or more optical opening(s) 15 located in brushhead 13, delivering radiation from optical opening(s) 15 to the oral areas being cleaned via the air gap between them. Radiation may also be delivered using passage 12, which terminates in brushhead 13 by being connected to one or more hollow bristle(s) 16 or one or more liquid opening(s) 17. In a preferred embodiment the PDT and the bleaching materials are introduced in liquids through passage 12.

Figure 2:
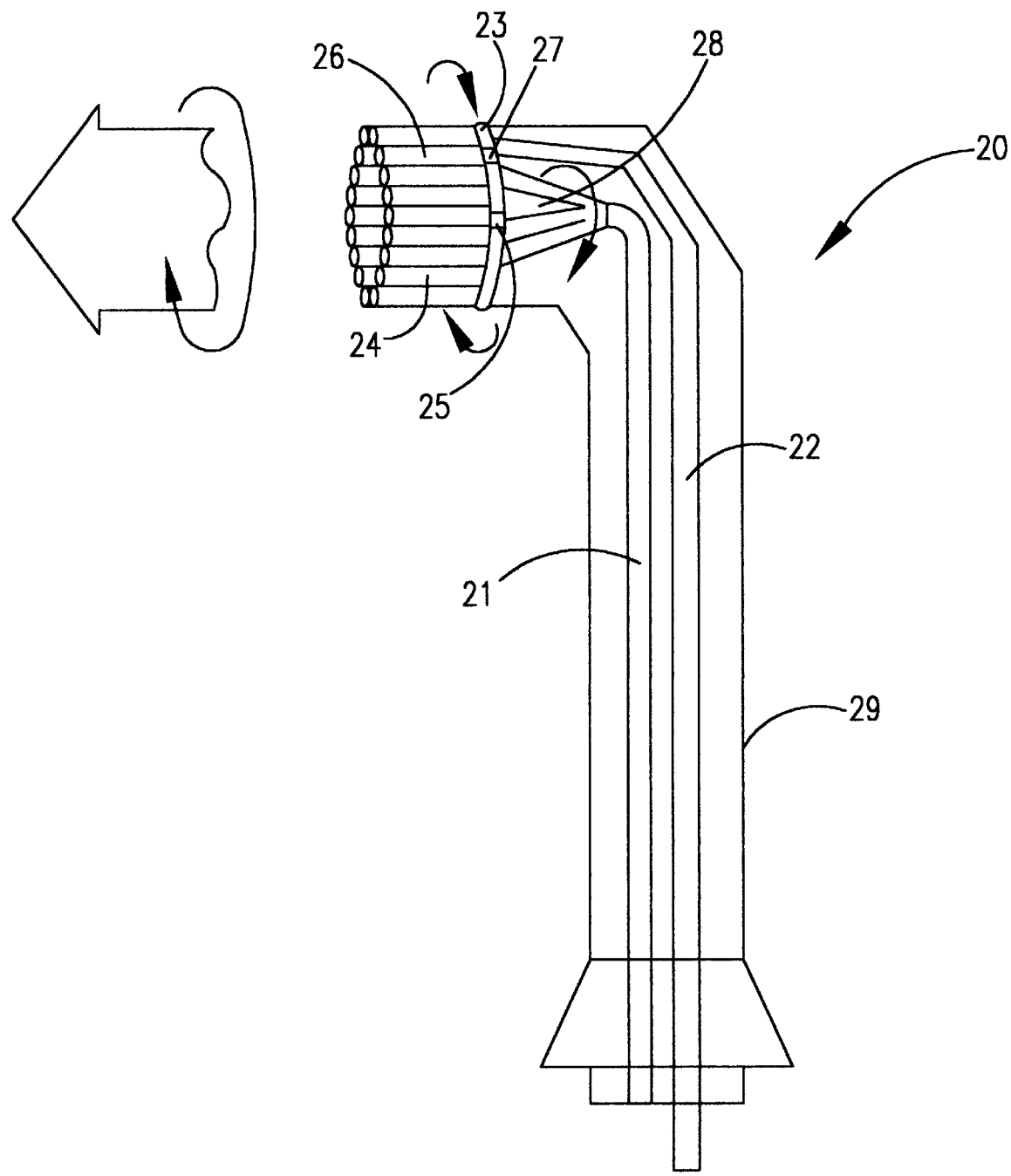
FIG. 2 is a view of the end of a mechanical oral cleaning system showing a circular rotating tip, optical fibers and liquid jets within the neck of the system for broader laser radiation delivery for use in the present invention.

FIG. 2 shows another preferred embodiment of a system to use with the invention in which plastic brush 20 is removable from handle 29, and has rotatable brushhead 23. Plastic brush 20 contains one or more optical fiber(s) 21 and water or liquid passage 22. Optical fiber 21 (or each optical fiber 21) carries radiation from a radiation source to rotatable optical connection 28, and water or liquid passage 22 carries water and/or a PDT/bleach containing liquid under pressure to rotatable brushhead 23. Optical fibers 21 may be optically connected to one or more optical bristle(s) 24 via optical connector 28, which deliver radiation to the areas in the mouth being cleaned through bristle 24 end not optically connected to optical connector 28. Optical fiber(s) 21 may also terminate in one or more optical opening(s) 25 located in rotatable brushhead 23, delivering radiation from optical opening(s) 25 to the oral areas being cleaned via the air gap between them. Radiation may also be delivered using a liquid going through passage 22. Passage 22 terminates at rotatable brushhead 23 and is connected to one or more hollow bristle(s) 26 or one or more liquid opening(s) 27. The liquid is delivered to the area to be cleaned or treated by passing through one or more hollow bristle(s) 26 or one or more liquid opening(s) 27.

Radiation is delivered by a pulsed diode laser or a continuous wave diode laser, to exactly where it is needed through plastic brush tips 10 or 20 in the normal course of tooth treatment.

Figure 3:
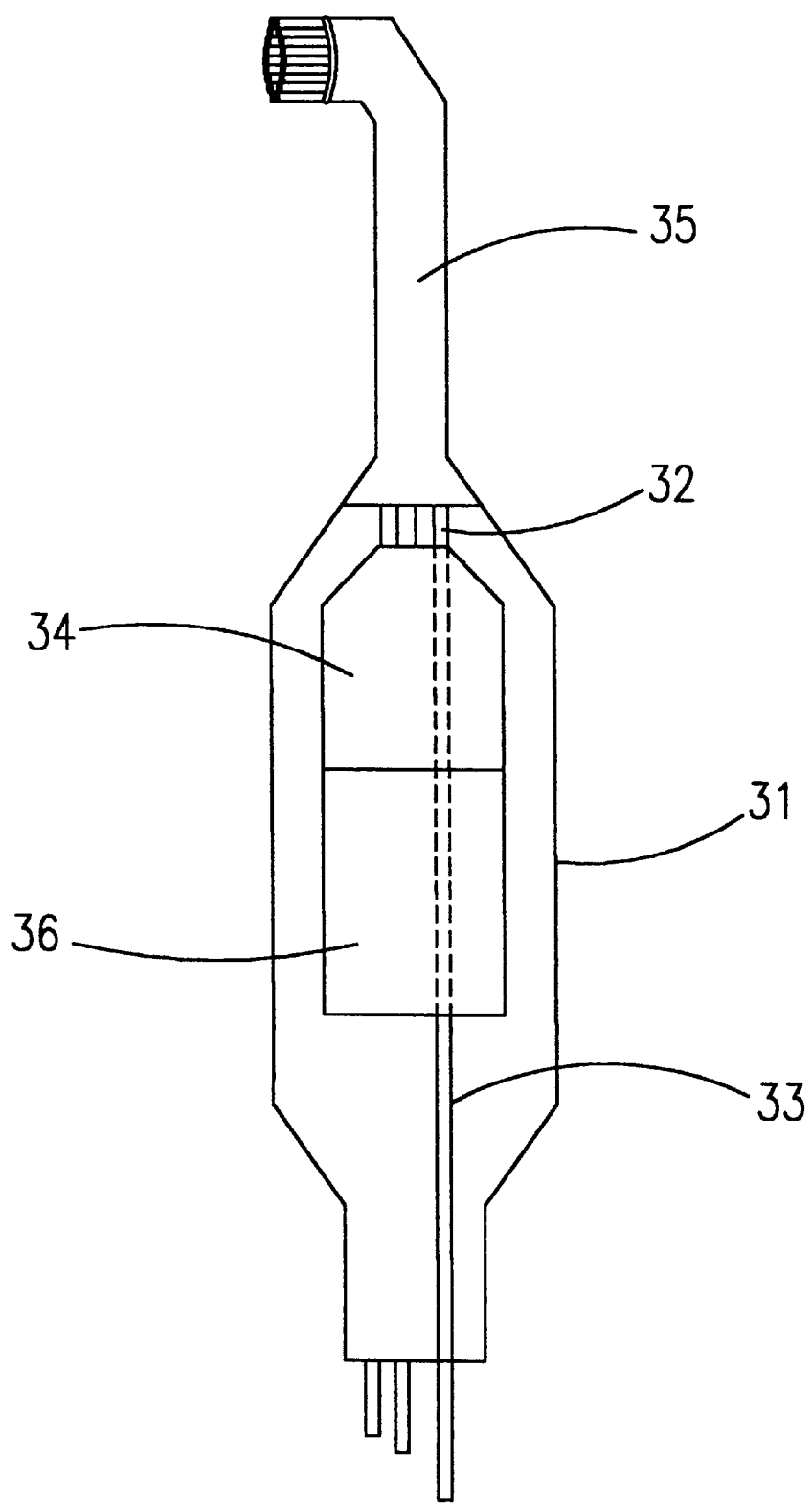
FIG. 3 is a sectional view of the mechanical oral cleaning system showing a brushhead, diode laser, power supply, cooling means and driver, which can be used in the present invention.

FIG. 3 shows handle means 31 containing diode laser 32 and electrical wiring 33, and cooling means 34 consisting of a Peltier cell. Radiation from diode laser 32 is delivered through replaceable brush 35. Handle means 31 may also contain battery cell or cells 36 which power diode laser 32.

Figure 4:
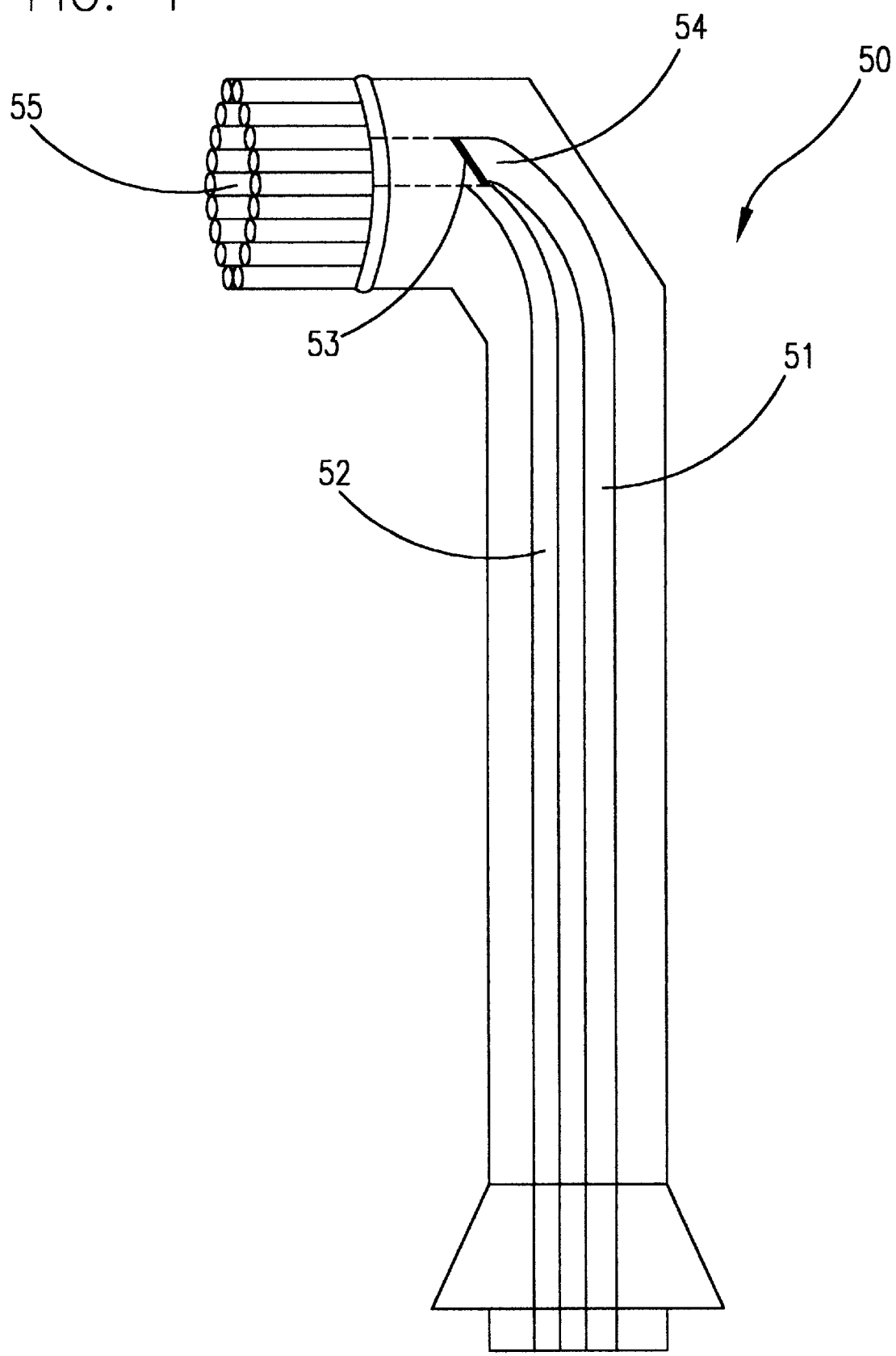
FIG. 4 is a view of a mechanical oral cleaning system with an optical fiber and a liquid jet, where the fiber optic's end terminates in at a safety-designed angle for use in the present invention.

FIG. 4 shows a preferred embodiment of a system to use with the invention in which plastic brush 50 contains optical fiber 51 and water or liquid passage 52. Optical fiber 51 carries radiation from a radiation source to fiber end 53, which terminates at designated angle 54 relative to optical fiber's 51 longitudinal axis. Water or liquid passage 52 carries water or a PDT/bleach containing liquid under pressure to fiber end 53. Water or liquid passes through passage 52, over surface of fiber end 53, and then through liquid and laser radiation delivery opening 55 to any proximal oral area to be cleaned or treated. Plastic brush 50 is designed to be safe for home use by the fact that laser radiation coming to fiber end 53 will be reflected harmlessly upward into plastic brush 50 if no liquid is being forced through liquid passage 52. This is due to angle 54 which creates a reflective surface because air and optical fiber 51 have substantially different n. When liquid is passing over the surface of fiber end 53 laser radiation will pass through substantially parallel to the longitudinal axis of optical fiber 51, thereby being delivered to oral areas to be cleaned or treated via opening 55 with the liquid that came through passage 52. This occurs because the difference in n between optical fiber 51 and a liquid or water is low enough that fiber end 53 is now a refractive, rather than a reflective, surface.

In the present invention, the dental laser brushing system is used in combination with a photosensitizer dental paste or liquid and possibly also a liquid or paste containing bleach.

Each of these would be either applied to the bristles of the device or if liquid introduced in the liquid stream. The photosensitizer liquid or paste when activated by an appropriate laser wavelength produces hyperactive singlet oxygen that destroys bacteria. The bleaching liquid or paste, if separate would be activated by an appropriate laser wavelength to degrade remnant photosensitizer before it caused staining of the teeth. The present invention uses low power laser energy, typically 2–3 mW, delivered by pulsed or by continuous wave action and a low concentration of photosensitizer for consumer use. The present invention guarantees good penetration of oral tissues.

As an example, using a laser toothbrush system as described in U.S. Pat. No. 5,658,148 having a laser operating at a wavelength of 670 nm and with a dental paste having a highly diluted quantity of Zn(II) phthalocyanine employing the following method would achieve significant reduction in bacteria over a week's practice of the invention. Paste applied to the bristles of the brushhead is worked into the crevices and gum line of the user's teeth. After a half a minute of spreading the paste over, between, etc. the teeth, the laser source is turned on and the safety mechanism deactivated. Keeping the same motion as used in spreading the paste the laser energy at about 2–3 mW is distributed over the dental area for a treatment period of about 1½ minutes. From a supply at the console a rinse, containing a small amount of bleaching species, travels through the laser toothbrush handle to the brushhead and onto the areas treated. The laser light continues to flood the area aiding in the bleaching process. Finally a clear water rinse is applied. Following this routine once a day over the week would lead to a reduced count of bacteria and other microbes in the vicinity of the teeth and gums. The user would find benefits of reduced incidence of dental caries, gum disease as well as aid in maintaining general health.

In a preferred embodiment of the invention, the method would use a laser toothbrush where the diode laser can be incorporated into the handle of the system together with its power supply and if necessary, with Peltier cells as a cooling system. Radiation from a diode laser source is delivered through one or more of the bristles on a replaceable brush that has a fixed or rotatable brushhead, or through liquid jets, or through openings in the brushhead corresponding to the radiation delivery medium. The diode laser would run on a battery or battery cells inside the handle. The replaceable brushes would have one of two types of brushheads:

(a) rotating bristles which are activated by applying the bristles to the oral surface or by the pressure of the flow of liquid through the jets;

(b) fixed bristles which are activated by applying the bristles to the oral surface or by the pressure of the flow of liquid through the liquid jets.

The rotating motion of the bristles, the pulsing action of the pulsed delivery, and/or the pressure of the liquid jets all increase the effectiveness of the system.

Also in a preferred embodiment of the invention, the method as described in the example above would use a system where the handle containing the diode laser is linked to a console by cable where there are electrical wires and small tubing for delivery of the dental liquid. The console contains all the necessary electronic components for operation of the dental laser brushing system. The console contains a container to hold the dental liquid or paste and its micropump. This dental liquid can be a dental paste, a pharmacological substance for medical treatment and/or a photosensitizer liquid for photodynamic-like therapy.

Also, in a particularly preferred embodiment the laser toothbrush used for the method would have the laser radiation from diode laser source delivered through the brushhead together with a liquid jet. Alternatively, the liquid jet itself can be the optical transfer medium for the radiation as the refractive index of water or the dental liquid is higher than that of air and as it is reasonably transparent for certain wave lengths applications to the procedure.

Having described the preferred embodiment of the invention with references to the accompanying drawings, it is to be understood that the invention is not limited to that precise embodiment and that various changes and modifications may be effected therein by one skilled in the art without departing from the scope or spirit of the invention as defined in the appended claims.

What is claimed is:

1. A safe, dental hygiene treatment method to be practiced by a user on a regularly scheduled basis, using a specially prepared dental liquid containing photosensitizer substances, which have specific absorption wavelengths, at concentration levels below that used in photodynamic therapy, and using photons at the absorption wavelengths delivered through a laser dental brushing device having a handle, a brushhead, at least one radiation source and access to a power source for said radiation source, delivery means for said radiation including a safety mechanism to prevent accidental radiation damage, means for applying a dental liquid containing said photosensitizers which on being irradiated at said wavelength create species in an immediate vicinity of said liquid capable of disinfecting an oral site, and comprising the steps of:

positioning said dental laser brushing device within one's mouth and deactivating said safety mechanism in said device;

applying said specially prepared dental liquid under sufficient liquid pressure to ensure that said dental liquid comes into close contact with all tissue and teeth to be treated, especially between individual teeth and along one's gum line, and using said brushhead to help disperse active ingredients within said dental liquid to further ensure said close contact;

producing in said laser dental brushing device a laser beam having substantially said specific wavelength, and delivering it at power levels no greater than 10 mW;

activating said photosensitizers with said specific wavelength to kill a portion of bacteria, germs, and microbes present on said tissue and teeth; and rinsing to remove excess material and by products of process.

2. A dental hygiene treatment method according to claim 1 wherein said step of rinsing is further characterized as including, degrading any colored remnants arising from said application of said dental liquid after said therapy is substantially completed, thereby enhancing brightness of teeth in contact with said photosensitizer substances.

3. The dental hygiene treatment method according to claim 2, wherein a bleaching agent is activated by a wavelength essentially equivalent to that of said radiation specific to said photosensitizer substances further comprising the step of:

applying said radiation beyond a therapeutic level so as to photo bleach said colored remnants and accomplish said bleaching step in claim 2.

4. The dental hygiene treatment method according to claim 2, wherein a bleaching agent is activated by a wavelength different from said radiation specific to said photosensitizer substances, further comprising the step of:

irradiating said bleaching agents with a radiation specific for said bleaching agent accomplish said bleaching step in claim 2.

5. A dental hygiene treatment method according to claim 1 wherein said specific wavelength is produced by a diode laser at a power level no greater than 5 mW.

6. A dental hygiene treatment method according to claim 5 further wherein said brushhead has a backing plate and a multiplicity of bristles, and provides access for said delivery means for said radiation.

7. A dental hygiene treatment method according to claim 6 wherein said diode laser is located in said brushhead and wherein delivering said specific wavelength radiation is done by a means selected from the group consisting of:

at least one optically conductive bristle firmly attached to said brushhead;

a pressurized water stream directed through said brushhead; and, an optical opening in said brushhead.

8. A dental hygiene treatment method according to claim 1, wherein said safety mechanism for said laser dental brushing device is derived from said delivery means for said radiation, which comprises an optical fiber optically connected to said radiation source, and where said optical fiber terminates such that said optical fiber's longitudinal axis is substantially directed at an opening in said brushhead, where said opening allows passage of liquid and radiation to oral areas to be treated, and where a tube provides passage for liquid under pressure, and where said optical fiber has a termination-tip which forms a substantially flat surface relative to said optical fiber's longitudinal axis, and where said tube has an open-end substantially near said termination-tip, and where liquid coming through said open-end passes over said surface of said termination-tip, and where an angle formed between said surface of said termination tip and said optical fiber's longitudinal axis forms a substantially refractive surface for said radiation while liquid is passing over said surface and then to said opening thereby passing said radiation substantially through said opening, and where said angle forms a substantially reflective surface for said radiation when said liquid is not passing over said surface, thereby stopping said radiation substantially at said brushhead.

9. A dental hygiene treatment method according to claim 1 wherein milder treatments can be used due to an increased efficiency of using a dental liquid having said photosensitizers loosely bound like an anti-body to a carrier species which helps said sensitizer to approach a bacteria's nucleus more closely.

10. A safe, dental hygiene treatment method to be practiced by a user on a regularly scheduled basis, using a specially prepared dental paste containing photosensitizer substances, which have specific absorption wavelengths, at concentration levels below that used in photodynamic therapy, and using photons at the absorption wavelengths delivered through a laser dental brushing device having a handle, a brushhead, at least one radiation source and access to a power source for said radiation source, delivery means for said radiation including a safety mechanism to prevent accidental radiation damage, means for applying a dental paste containing said photosensitizers which on being irradiated at said wavelength create species in an immediate vicinity of said liquid capable of disinfecting an oral site, and comprising the steps of:

positioning said dental laser brushing device within one's mouth and deactivating said safety mechanism in said device;

applying said specially prepared dental paste using said brushhead to help disperse active ingredients within said dental paste to ensure that said dental paste comes into close contact with all tissue and teeth to be treated, especially between individual teeth and along one's gum line;

producing in said laser dental brushing device a laser beam having substantially said specific wavelength, and delivering it at power levels no greater than 10 mW;

activating said photosensitizers with said specific wavelength to kill a portion of bacteria, germs, and microbes present on said tissue and teeth; and rinsing to remove excess material and by products of process.

11. A dental hygiene treatment method according to claim 10 wherein said step of rinsing is further characterized as including, degrading any colored remnants arising from said application of said dental paste after said therapy is substantially completed, thereby enhancing brightness of teeth in contact with said photosensitizer substances.

12. A dental hygiene treatment method according to claim 11 further wherein said brushhead has a backing plate and a multiplicity of bristles, and provides access for said delivery means for said radiation.

13. A dental hygiene treatment method according to claim 12 wherein said diode laser is located in said brushhead and wherein delivering said specific wavelength radiation by a means selected from the group consisting of:

at least one optically conductive bristle firmly attached to said brushhead;

a pressurized water stream directed through said brushhead; and, an optical opening in said brushhead.

14. The dental hygiene treatment method according to claim 11, wherein a bleaching agent is activated by a wavelength essentially equivalent to that of said radiation specific to said photosensitizer substances further comprising the step of:

applying said radiation beyond a therapeutic level so as to photo bleach said colored remnants and accomplish said bleaching step in claim 10.

15. The dental hygiene treatment method according to claim 11, wherein a bleaching agent is activated by a wavelength different from said radiation specific to said photosensitizer substances, further comprising the step of:

irradiating said bleaching agents with a radiation specific for said bleaching agent accomplish said bleaching step in claim 10.

16. A dental hygiene treatment method according to claim 10 wherein said specific wavelength is produced by a diode laser at a power level no greater than 5 mW.

17. A dental hygiene treatment method according to claim 10, wherein said safety mechanism for said laser dental brushing device is derived from said delivery means for said radiation, which comprises an optical fiber optically connected to said radiation source, and where said optical fiber terminates such that said optical fiber's longitudinal axis is substantially directed at an opening in said brushhead, where said opening allows passage of liquid and radiation to oral areas to be treated, and where a tube provides passage for liquid under pressure, and where said optical fiber has a termination-tip which forms a substantially flat surface relative to said optical fiber's longitudinal axis, and where said tube has an open-end substantially near said termination-tip, and where liquid coming through said open-end passes over said surface of said termination-tip, and where an angle formed between said surface of said termination tip and said optical fiber's longitudinal axis forms a substantially refractive surface for said radiation while liquid is passing over said surface and then to said opening thereby passing said radiation substantially through said opening, and where said angle forms a substantially reflective surface for said radiation when said liquid is not passing over said surface, thereby stopping said radiation substantially at said brushhead.

18. A dental hygiene treatment method according to claim 10 wherein milder treatments can be used due to an increased efficiency of using a dental liquid having said photosensitizers loosely bound like an antibody to a carrier species which helps said sensitizer to approach a bacteria's nucleus more closely.

* * * * *